(12) United States Patent
Makhlouche et al.

(10) Patent No.: US 11,154,733 B2
(45) Date of Patent: Oct. 26, 2021

(54) RESPIRATORY PROTECTION HOOD

(71) Applicant: L'Air Liquide, Societe Anonyme pour l'Etude et l'Exploitation des Procedes Georges Claude, Paris (FR)

(72) Inventors: Rachid Makhlouche, Grenoble (FR); Jean-Michel Cazenave, Seyssins (FR); Xavier Roussin-Bouchard, Meaudre (FR); Pierrick Cohard, Les Abrets (FR); Vincent Graziani, Chabons (FR)

(73) Assignee: L'Air Liquide Société Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 505 days.

(21) Appl. No.: 15/768,369

(22) PCT Filed: Oct. 5, 2016

(86) PCT No.: PCT/FR2016/052553
§ 371 (c)(1),
(2) Date: Apr. 13, 2018

(87) PCT Pub. No.: WO2017/064393
PCT Pub. Date: Apr. 20, 2017

(65) Prior Publication Data
US 2018/0296863 A1    Oct. 18, 2018

(30) Foreign Application Priority Data
Oct. 15, 2015   (FR) ...................................... 1559783

(51) Int. Cl.
*A62B 17/04*   (2006.01)
*A62B 19/00*   (2006.01)
(Continued)

(52) U.S. Cl.
CPC ................ *A62B 17/04* (2013.01); *A62B 7/10* (2013.01); *A62B 19/00* (2013.01);
(Continued)

(58) Field of Classification Search
CPC .......... A62B 17/04; A62B 19/00; A62B 19/02
See application file for complete search history.

(56) References Cited

U.S. PATENT DOCUMENTS 5,495,847 A *  3/1996  Hu ......................... A62B 17/04
                                                 128/201.22
5,724,958 A    3/1998  Farnworth et al.
(Continued)

FOREIGN PATENT DOCUMENTS

| EP | 2 979 561 | 2/2016 |
| FR | 2 582 524 | 12/1986 |
| WO | WO 90/00421 | 1/1990 |

OTHER PUBLICATIONS

International Search Report and Written Opinion for PCT/FR2016/052553, dated Jan. 23, 2017.
(Continued)

*Primary Examiner* — LaToya M Louis
(74) *Attorney, Agent, or Firm* — Christopher J. Cronin (57) ABSTRACT

A respiratory protection hood having a sealed flexible shell including a pressurized oxygen vessel provided with a calibrated output opening leading into the inside space of the flexible shell and a device for trapping at least one portion of the carbon dioxide exhaled by the user that includes a cartridge for adsorbing carbon dioxide having a perforated tube arranged around a volume of carbon dioxide absorbing material. At least one portion of the perforated tube being arranged around the volume of absorbent material in direct communication with the inside space of the hood.

17 Claims, 4 Drawing Sheets

(51) Int. Cl.
- *A62B 7/10* (2006.01)
- *A61M 16/22* (2006.01)
- *A62B 7/02* (2006.01)
- *A62B 7/14* (2006.01)
- *A61M 16/06* (2006.01)
- *B63C 11/24* (2006.01)

(52) U.S. Cl.
CPC ......... *A61M 16/0627* (2014.02); *A61M 16/22* (2013.01); *A61M 2202/0208* (2013.01); *A62B 7/02* (2013.01); *A62B 7/14* (2013.01); *B63C 11/24* (2013.01)

(56) References Cited

U.S. PATENT DOCUMENTS

| | | | |
|---|---|---|---|
| 6,279,571 B1* | 8/2001 | Meckes | A62B 7/02 128/201.22 |
| 7,520,280 B2 | 4/2009 | Gordon | |
| 2010/0242966 A1 | 9/2010 | Johnson | |
| 2011/0226240 A1* | 9/2011 | Navalesi | A61M 16/06 128/201.23 |

OTHER PUBLICATIONS

French Search Report and Written Opinion for FR 1 559 783, dated Aug. 26, 2016.

* cited by examiner

RESPIRATORY PROTECTION HOOD

CROSS-REFERENCE TO RELATED APPLICATIONS

This application is a § 371 of International PCT Application PCT/FR2016/052553, filed Oct. 5, 2016, which claims § 119(a) foreign priority to French patent application FR 1 559 783, filed Oct. 15, 2015.

BACKGROUND

Field of the Invention

The invention relates to a respiratory protection hood.

The invention relates more particularly to a respiratory protection hood comprising a sealed flexible envelope intended to be fitted over the head of a user, the flexible envelope being provided with a transparent window and comprising, in its lower part, a rigid base element intended to be arranged around the neck of the user, the base element comprising a pressurized oxygen reservoir provided with a calibrated outlet orifice opening into the internal volume of the flexible envelope and a device for capturing at least part of the carbon dioxide exhaled by the user, in order to purify the breathable gas within the hood.

Related Art

This type of equipment is generally mandatory on board civilian passenger transport aircraft and in certain military transport aircraft. Reference may be made for example to document FR2582524A1.

The invention relates in particular to respiratory protection equipment operating in a closed circuit. This type of closed-circuit operation makes it possible to minimize the bulk and the mass of an item of respiratory equipment. To achieve this, the equipment must comprise a sealed volume (hood envelope) around the head of the user in which oxygen is released and the concentration of carbon dioxide maintained at a defined low level. Typically, the percentage of carbon dioxide must remain below 4% (at sea level).

To maintain this low level of carbon dioxide, one solution is to provide in the hood a device for capturing carbon dioxide, for example a cartridge for absorbing carbon dioxide (CO2).

Cartridges of radial structure are known for their purification efficiency and the low pressure drop that they generate. Radial cartridges optimize the gas residence time in the cartridge (and therefore the efficiency of the purification). However, this type of cartridge is generally very bulky and not very ergonomic (cf. for example US2010242966A or U.S. Pat. No. 7,520,280).

In particular, these cartridges need to have a gas collector and a gas diffuser of sufficient cross sections to limit the pressure drop. Moreover, the need to provide a sufficient filtering material volume can rapidly lead to a significant outside diameter of the cartridge. The length of the known devices, although beneficial in terms of the gas residence time and the pressure drop, makes the ergonomic integration of the cartridge into an item of respiratory protection equipment more difficult.

SUMMARY OF THE INVENTION

An aim of the present invention is to overcome all or some of the disadvantages of the prior art outlined above.

To this end, the hood according to the invention, which in other respects conforms to the generic definition given of it in the preamble above, is essentially characterized in that the device for capturing carbon dioxide comprises a cartridge for adsorbing carbon dioxide of radial structure comprising a tubular body extending in a longitudinal direction and accommodating a volume of material which absorbs carbon dioxide, said structure of the cartridge comprising a perforated tube arranged around the volume of absorbent material and extending in the longitudinal direction to allow air to be purified to transit radially into the volume of absorbent material, that is to say perpendicularly to the longitudinal direction, and in that at least part of the perforated tube arranged around the volume of absorbent material communicates directly with the internal volume of the hood, that is to say that at least part of the perforated tube is not surrounded by a solid additional outer wall delimiting a diffusing volume around the perforated tube.

Moreover, embodiments of the invention can comprise one or more of the following features:
- the perforated tube comprises a perforated outer wall and a perforated inner wall, the volume of absorbent material being arranged between inner and outer walls,
- the purified air having transited into the volume of absorbent material is collected in a purified-air collecting volume, at least part of the purified-air collecting volume being delimited by the inner wall of the perforated tube,
- at least part of the peripheral surface of the perforated tube comprises projections extending radially toward the outside of the perforated tube with respect to the longitudinal axis in order to prevent the flexible envelope or the skin of the user from obstructing the orifices of the perforated tube,
- the projections extend radially with respect to the longitudinal axis with a height of between 1 and 5 mm with respect to the remainder of the peripheral surface of the perforated tube,
- the tube comprises projections distributed along the longitudinal direction, the projections being space apart from one to the other in the longitudinal direction by a distance of between 10 mm and 50 mm,
- the tube comprises projections distributed over at least part of and preferably over all its circumference,
- the tube comprises projections forming longitudinal ribs parallel to the longitudinal axis,
- the tube comprises projections forming transverse ribs perpendicular to the longitudinal axis,
- the perforated tube comprises a plurality of orifices provided for the passage of gas, said orifices having areas of between 3.14 mm$^2$ and 600 mm$^2$,
- the perforated tube comprises on its surface a plurality of orifices of circular and/or oblong and/or trapezoidal shape, said elongate orifices being parallel or perpendicular to the longitudinal direction,
- the perforated tube is composed of a grid-like metal or plastic structure,
- the perforated tube is composed of a base structure comprising a skeleton covered by a perforated sheet, in particular by a perforated plastic sheet fixed to the base structure,
- the perforated sheet is made of plastic and is adhesively bonded to or overmolded on the base structure,
- the perforated tube is curved or rectilinear.

The invention may also relate to any alternative device or method comprising any combination of features above or below.

Other particular features and advantages will become apparent from reading the description which follows with reference to the figures, in which:

DETAILED DESCRIPTION OF THE INVENTION

Figure 1:
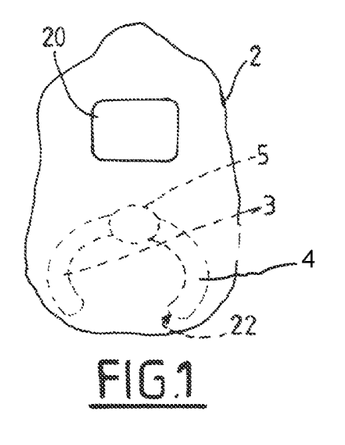
FIG. 1 represents a partial schematic front view, partly in phantom, illustrating the structure of one possible exemplary embodiment of a hood according to the invention.

The nonlimiting example of a respiratory protection hood represented in FIG. 1 comprises a sealed flexible envelope 2 intended to be fitted over the head of a user.

Preferably, flexible envelope 2 is provided with a transparent window 20 and comprising, in its lower part, a rigid base element 3, 4 intended to be arranged around the neck of the user.

The sealed flexible envelope 2 is composed for example of a flame-retardant textile which is sealed or rendered sealed. For example, this is a textile of synthetic fibers of low combustibility.

Figure 2:
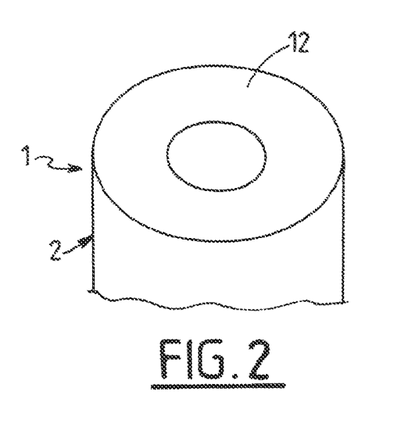
FIG. 2 represents a bottom view of a detail of the hood of FIG. 1.

This envelope 2 is intended to be fitted over the head of the user to isolate the head of the user from the external surroundings and to integrate the functionalities described below. To achieve sealing at the neck of the user, and as described in FIG. 2, the base of the flexible envelope 2 can comprise a flexible diaphragm or a sealed collar 12 intended to be mounted around the neck of a user. For example, this lower collar 12 comprises a pierced sheet of plastic (for example a polymer, in particular a self-extinguishing polymer such as neoprene or silicone) in order to elastically let through the head of the user and then tighten around his neck afterwards. The lower orifice for the head can be adapted to any neck perimeter of between 28 and 42 cm, for example.

The base element 3, 4 comprises a pressurized oxygen reservoir 3 provided with a calibrated outlet orifice 7 opening into the internal volume of the flexible envelope 2 and a device for capturing at least part of the carbon dioxide exhaled by the user. The device for capturing CO2 is intended for purifying the breathable gas within the hood 2 to maintain the level of CO2 below a defined threshold.

As schematically illustrated, the base element 3, 4 can, where appropriate, be made up of at least two articulated parts (articulation 5).

The device for capturing CO2 comprises a cartridge 4 for adsorbing carbon dioxide. The cartridge 4 comprises a tubular body extending in a longitudinal direction A and accommodating a volume 8 of material which absorbs carbon dioxide. This cartridge 4 is of radial structure. That is to say that the structure of the cartridge 4 comprising a perforated tube 9 arranged around the volume 8 of absorbent material and extending in the longitudinal direction A to allow air to be purified to transit radially into the volume 8 of absorbent material. That is to say that the gas to be purified passes through the filter cartridge perpendicularly to the longitudinal direction A.

According to one particular advantageous feature, at least part of the perforated tube 9 arranged around the volume of absorbent material communicates directly with the internal volume of the hood 2. That is to say that at least part of the perforated tube 9 (that is to say the holed wall) is not surrounded by a solid additional outer wall delimiting a diffusing volume around the perforated tube 9.

This structure improves the mass, the volume and the operation of the hood and in particular its system for capturing CO2.

Conventionally, radial CO2-absorption cartridges comprise radially from the inside to the outside: a central core collecting the purified gas, a mass of CO2-adsorbing material arranged around the central core and arranged in a perforated tubular wall, and an outer solid wall arranged around the perforated tubular wall. The gas to be purified enters through one end of the cartridge and circulates in the space (called "distributor" or "diffuser") between the outer solid wall and the perforated tubular wall. The gas to be purified enters the CO2-adsorbing material radially (via the holes of the perforated wall) and exits purified in the central core (via holes). That is to say that the central core forms a purified-gas collector toward an outlet at one end of the cartridge.

The positions of the purified-gas collector and of the distributor can optionally be interchanged (that is to say that the gas enters through the central core and the cartridge and exits through the periphery while transiting radially from the inside to the outside instead of vice versa).

According to the invention, the outer wall delimiting the distributor is dispensed with. This makes it possible to reduce the volume and the mass of the device, enabling it to be integrated into a hood. In particular, this structure, without harming the efficiency of the device, makes it possible for example to reduce the outside diameter of the cartridge by about 20 mm (from a total typically of 90 mm in known solutions).

This simplification is possible due to the fact that the cartridge (perforated wall) is directly integrated into the breathable volume of gas to be purified.

That is to say that the gas to be purified is directly admitted through holes of the perforated wall into the cartridge 4.

Figure 5:
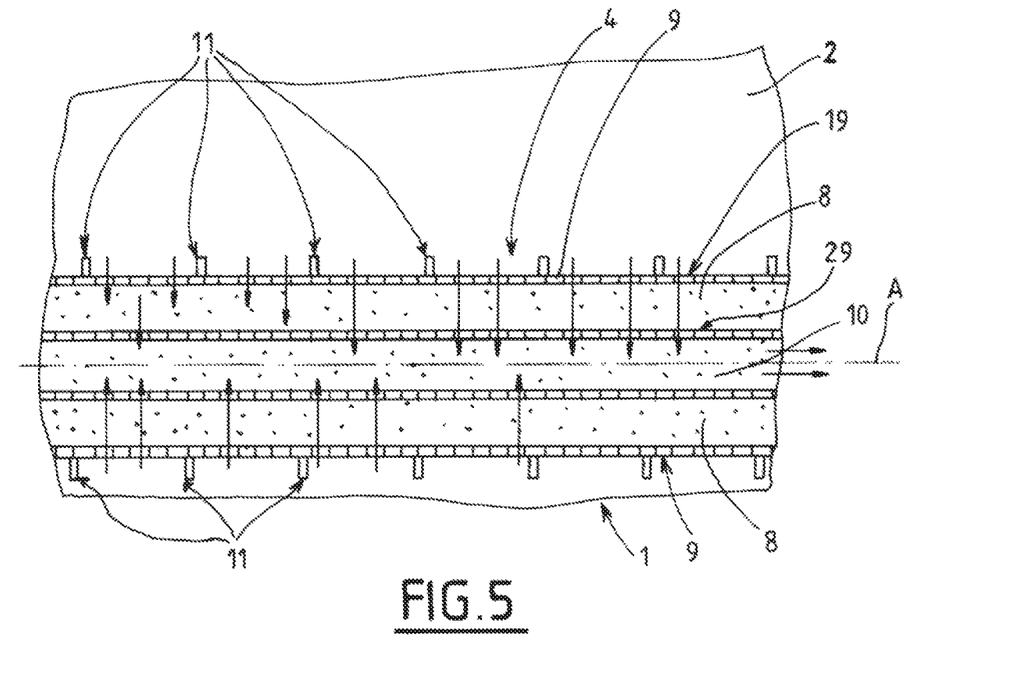
FIG. 5 represents a partial schematic sectional view of a detail of a hood according to the invention, illustrating the structure of a device for capturing CO2 according to the invention.

FIG. 5 illustrates an exemplary embodiment explaining this structure.

The cartridge 4 comprises a structure with a perforated tube 9. This perforated tube comprises a perforated outer wall 19, which is for example cylindrical, and a perforated inner wall 29, which is for example cylindrical also and concentric.

The volume 8 of material which absorbs CO2 is arranged and held between the inner 29 and outer 19 walls. The inner wall 29 communicates with a central volume 10 forming a path for the evacuation of the purified gas (cf. also FIG. 9).

That is to say that the perforated outer wall 19 (provided with holes) communicates directly with the gas in the envelope 2. The gas path is schematically illustrated in FIG. 5 via arrows.

In order, where appropriate, to prevent the flexible envelope 2 from closing off the inlet orifices in the cartridge 4, as illustrated in FIG. 5, the peripheral surface of the perforated tube 9 can comprise one or more projections 11 which extend radially toward the outside of the perforated tube 9 with respect to the axis A.

These projections 11 form "spacers" that make it possible to prevent the flexible envelope 2 or the skin of the user from obstructing the orifices of the perforated tube 9 by preventing a sealed contact against the perforated wall 19.

The projections 11 also make it possible to prevent the skin of the user coming into contact with the grid containing the CO2-adsorbing material 8 since, generally, the CO2 binding reaction is exothermic (the temperature of the cartridge can reach 40° C., which would be uncomfortable).

The projections 11 extend radially with respect to the longitudinal axis A with a height of, for example, between 1 mm and 5 mm with respect to the remainder of the peripheral surface of the perforated tube 9.

The projections 11 are preferably distributed along the longitudinal direction A. The projections 11 can be space apart from one to the other in the longitudinal direction A by a distance of, for example, between 1 mm and 50 mm.

The projections 11 can be distributed over at least part of and preferably over all the circumference of the perforated tube 9.

Figure 9:
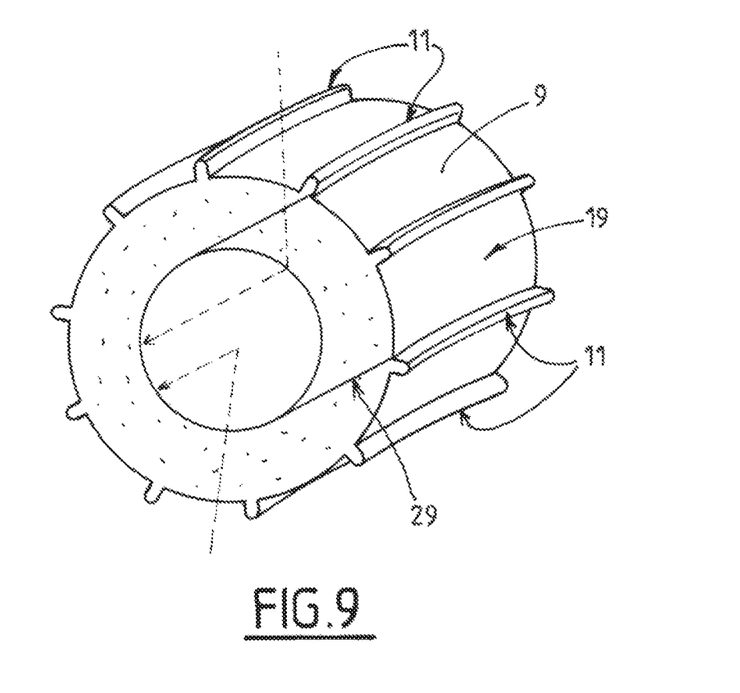
FIG. 9 represents a schematic perspective cross-sectional view of a detail of an example of a structure of a cartridge which absorbs CO2 according to the invention.

As illustrated in FIG. 9, the projections 11 can form longitudinal ribs parallel to the longitudinal axis A of the perforated tube 9.

Figure 6:
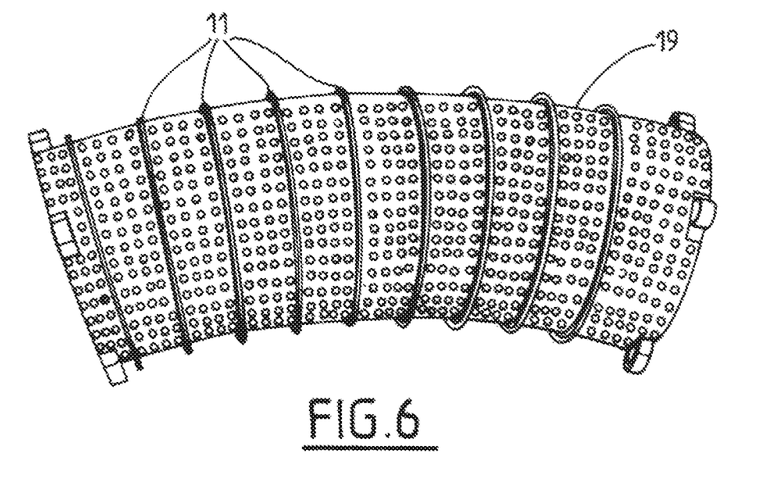
FIG. 6 represents a perspective view of a detail of the perforated outer wall of a cartridge for absorbing CO2 according to the invention.

As illustrated in FIG. 5 or 6, the projections 11 can form transverse ribs (rings) perpendicular to the longitudinal axis A of the perforated tube 9.

Instead of (or in addition to) projections 11 in the form of ribs, the projections 11 can be discrete studs distributed over the perforated wall 19.

As illustrated in FIGS. 1, 6, 7 and 8, the reservoir 3 and/or the cartridge 4 and thus the perforated tube 9 can be curved in order to improve the integration thereof around the head or the neck of the user. This curving can be continuous (cf. FIGS. 6 and 7) or obtained by rectilinear portions assembled with an angle (cf. FIG. 8).

Preferably however, the filter cartridge 4 is rectilinear (cylindrical tube of which the longitudinal direction A is rectilinear, that is to say noncurved).

Moreover, the oxygen reservoir 3 is for its part preferably curved (curved longitudinal axis).

Conventionally, the CO2-adsorbing material 8 can comprise, for example, soda lime ($Ca(OH)_2$) or lithium hydroxide (LiOH). These materials both react with $CO_2$ to generate a carbonate compound, water and heat.

These materials are generally used in the form of granules of different diameters packaged in radial or axial cartridges but sometimes also in the form of a sheet (shaped paste) or of a mat (granules contained in a porous envelope). For example, the material 8 is housed in the perforated tube 9 and held therein via stoppers mounted at the ends of the tube 9. The stopper of the radial cartridge can be a simple stopper or can have a function of tamping the material 8 with metal springs or a plastic part which is deformable under stress.

Figure 3:
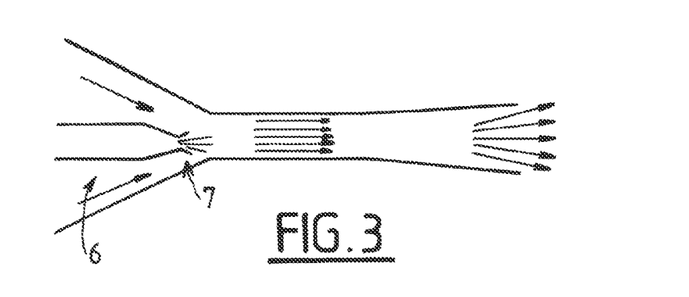
FIG. 3 illustrates an example of a venturi-effect gas-injection device which can be employed in the hood according to the invention.
Figure 4:
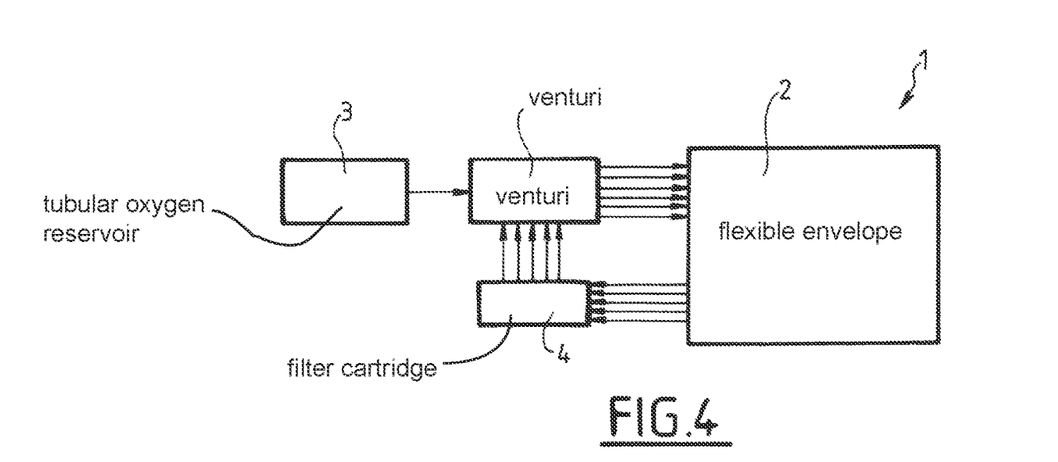
FIG. 4 represents a schematic view illustrating the integration and the operation of the gas-injection device in the hood according to the invention.

FIGS. 3 and 4 schematically illustrate one possible arrangement of the system for generating breathable gas in the hood 2.

As illustrated in FIG. 3, the outlet orifice 7 of the tubular oxygen reservoir 3 and the filtered-air outlet 6 of the filtration cartridge 4 can be arranged relatively (in particular concentrically and coaxially) to form a venturi device.

FIG. 4 schematically illustrates the gas flows via arrows. The oxygen is supplied by the oxygen reservoir 3 to the venturi which then generates suction through the filter cartridge 4. The oxygen-enriched breathable mixture is delivered into the flexible envelope 2. This venturi device thus makes it possible to use the energy of expansion of the gas supplied by the pressurized reservoir 3 to create a recirculation stream through the filter cartridge 4 (soda lime or lithium hydroxide). Preferably, the venturi has an entrainment ratio (aspirated flow rate/injected flow rate) of between 10 and 20 over the range of injected flow rates of from 1 to 5 liters per minute for example.

The perforated tube 9 containing the filter entity 8 preferably has a grid-shaped structure (made of plastic or metal or some other material).

Figure 7:
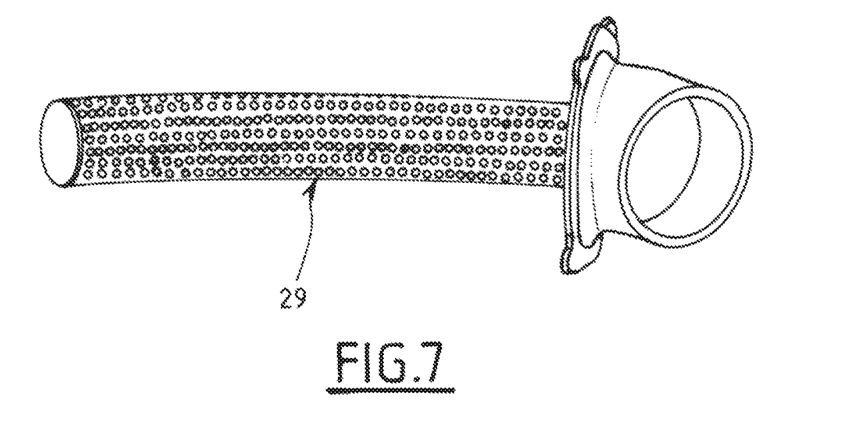
FIG. 7 represents a perspective view of a detail of the perforated inner wall of a cartridge for absorbing CO2 according to the invention connected to an outlet collector.

As illustrated in FIGS. 6 and 7, this structure can be a structure of the rigid grid type provided with circular holes.

Figure 8:
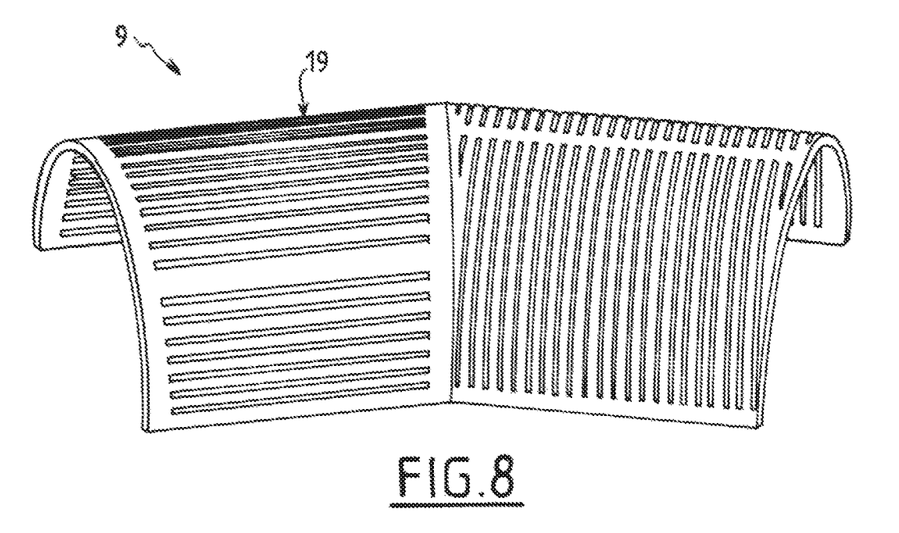
FIG. 8 represents a perspective view of a detail of another possible exemplary embodiment of the structure of the perforated wall of a cartridge for absorbing CO2 according to the invention.

As illustrated in FIG. 8, this structure can be a structure of the rigid grid type provided with holes in the form of slots (longitudinal slots; cf. left-hand part, and/or transverse slots; cf. right-hand part). This structure 9 can be molded, for example.

Figure 10:
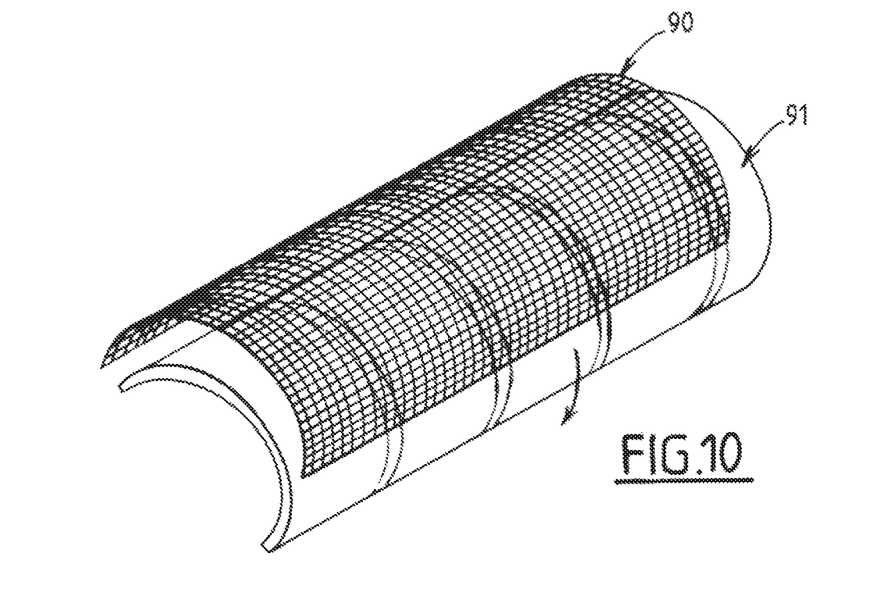
FIG. 10 represents a perspective view of a detail of another possible exemplary embodiment for realizing the structure of the perforated wall of a cartridge for absorbing CO2 according to the invention.

FIG. 10 illustrates another exemplary embodiment of the perforated tube 9. It can be composed of a base structure 91 comprising a skeleton covered with a perforated sheet 90, in particular by a perforated plastic sheet 90 fixed to the base structure 91. The base structure 91 is produced by plastic injection-molding, for example. The base structure 91 can also integrate projections ("spacers").

For example, the gridding function (perforated wall provided with gas passage orifices) can be realized by a plastic sheet 90 having a structure resembling that of a mosquito net (made of polyamide with orifices having a size of between 20 and 200 μm).

The perforated tube 9 preferably comprises a plurality of orifices intended for the passage of gas, said orifices having areas of between 3.14 $mm^2$ and 600 $mm^2$. For example, the bottom value of 3.14 $mm^2$ can correspond to the case where the cartridge will comprise a multitude of circular orifices of 1 mm radius. Likewise, the top value of 600 $mm^2$ can correspond to the case where the structure of the tube would serve only as a skeleton for a sheet of the mosquito net type affixed to this skeleton structure. This skeleton would have, for example, openings (rectangular or of other form) with a dimension of 6×100 $mm^2$, for example.

The radial geometry of the cartridge 4 makes it possible to maximize the length of the volume of CO2-adsorbing material 8 and thus makes it possible to reduce the height of the bed of porous entity to be traversed. This makes it possible to reduce the outside diameter of the cartridge 4, while improving the residence time and the pressure drop of the gas to be purified. This is thus compatible with the storage space requirement aimed at for this type of equipment in aircraft.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing i.e. anything else may be additionally included and remain within the scope of "comprising." "Comprising" is defined herein as necessarily encompassing the more limited transitional terms "consisting essentially of" and "consisting of"; "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

What is claimed is:

1. A respiratory protection hood comprising a sealed flexible envelope intended to be fitted over the head of a user, the flexible envelope being provided with a transparent window and comprising, in a lower part thereof, a rigid base element intended to be arranged around a neck of the user, the base element comprising a pressurized oxygen reservoir provided with a calibrated outlet orifice opening into an internal volume of the flexible envelope and a cartridge for capturing at least part of the carbon dioxide exhaled by the user in order to purify breathable gas within the hood, wherein:

the cartridge comprises a tubular body extending in a longitudinal direction between two ends, a cylindrical perforated outer wall, a cylindrical perforated inner wall concentrically disposed within the cylindrical perforated outer wall, and a volume of material which absorbs carbon dioxide disposed between the cylindrical perforated outer wall and the cylindrical perforated inner wall; a configuration of the cartridge allowing:

air to be purified to transit through the cylindrical perforated outer wall and into the volume of absorbent material in a radial direction that is perpendicular to the longitudinal direction, purified air to radially transit through the cylindrical perforated inner wall and out of the volume of absorbent material and into a hollow space enclosed by the cylindrical perforated inner wall, and the purified air within the hollow space enclosed by the cylindrical perforated inner wall to be evacuated in the longitudinal direction from one of the ends of the cartridge; the perforated tube having orifices; and at least part of the cylindrical perforated outer wall arranged communicates directly with the internal volume of the hood so that at least part of the cylindrical perforated outer wall is not surrounded by a solid additional outer wall delimiting a diffusing volume around the cylindrical perforated outer wall.

2. The respiratory protection hood of claim 1, wherein the perforated tube comprises a perforated outer wall and a perforated inner wall, the volume of absorbent material being arranged between the inner and outer walls.

3. The respiratory protection hood of claim 2, wherein the purified air having transited into the volume of absorbent material is collected in a purified-air collecting volume, at least part of the purified-air collecting volume being delimited by the inner wall of the perforated tube.

4. The respiratory protection hood of claim 1, wherein at least part of the peripheral surface of the perforated tube comprises projections which extend radially outward with respect to the longitudinal axis so that the flexible envelope and any skin of the user is prevented from obstructing the orifices of the perforated tube.

5. The respiratory protection hood of claim 4, wherein the projections extend radially to a height of between 1 and 5 mm.

6. The respiratory protection hood of claim 4, wherein the projections are distributed along the longitudinal direction and spaced apart from one another in the longitudinal direction by a distance between 10 mm and 50 mm.

7. The respiratory protection hood of claim 4, wherein the projections are distributed over at least part of a circumference of the perforated tube.

8. The respiratory protection hood of claim 4, wherein the projections are distributed over all a circumference of the perforated tube.

9. The respiratory protection hood of claim 4, wherein the projections include longitudinal ribs that extend parallel to the longitudinal axis.

10. The respiratory protection hood of claim 4, wherein the projections include transverse ribs that extend perpendicular to the longitudinal axis.

11. The respiratory protection hood of claim 1, wherein the orifices of the perforated tube have areas of between 3.14 $mm^2$ and 600 $mm^2$.

12. The respiratory protection hood of claim 1, wherein the orifices have a circular and/or oblong and/or trapezoidal shape, said orifices being parallel or perpendicular to the longitudinal direction.

13. The respiratory protection hood of claim 12, wherein the orifices are elongate and have an oblong and/or trapezoidal shape, said elongate orifices extending in a direction parallel or perpendicular to the longitudinal direction.

14. The respiratory protection hood of claim 1, wherein the perforated tube is comprised of a grid-like metal or plastic structure.

15. The respiratory protection hood of claim 1, wherein the perforated tube has a base structure comprising a skeleton that is covered by a perforated sheet.

16. The respiratory protection hood of claim 1, wherein the perforated tube has a base structure comprising a skeleton that is covered by a perforated plastic sheet fixed to the base structure.

17. The respiratory protection hood of claim 16, wherein the perforated plastic sheet is adhesively bonded to or overmolded on the base structure.

* * * * *